… …

United States Patent

Jahanger

Patent Number: 5,997,548
Date of Patent: Dec. 7, 1999

[54] UMBILICAL CORD CUTTING AND CLAMPING DEVICE

[76] Inventor: Mohammed S. Jahanger, 440 Egg Harbor Rd., Turnersville, N.J. 08012

[21] Appl. No.: 09/120,425

[22] Filed: Jul. 22, 1998

[51] Int. Cl.$^6$ .................................................. A61B 17/42
[52] U.S. Cl. ............................................................ 606/120
[58] Field of Search ..................... 606/120, 157, 606/142, 167, 174, 210, 205, 211

[56] References Cited

U.S. PATENT DOCUMENTS

| | | | |
|---|---|---|---|
| 4,428,374 | 1/1984 | Auburn | 606/120 |
| 4,870,965 | 10/1989 | Jahanger | 606/120 |
| 5,009,657 | 4/1991 | Cotey et al. | 606/120 |
| 5,127,915 | 7/1992 | Mattson | 606/120 |
| 5,797,922 | 8/1998 | Hessel et al. | 606/120 |

Primary Examiner—Michael Buiz
Assistant Examiner—Tan-uyen Thi Ho
Attorney, Agent, or Firm—Paul and Paul

[57] ABSTRACT

An umbilical cord cutting and clamping device includes a pair of opposed jaws with a blade mounted in one jaw, and the other jaw has teeth spaced along the inner surface for grasping the umbilical cord. The jaw carrying the blade include two grasping teeth on each side of the blade and at its inner end, so that the upper surface can be smoothly cut as the device is closed secondary to flattening the cord.

14 Claims, 4 Drawing Sheets

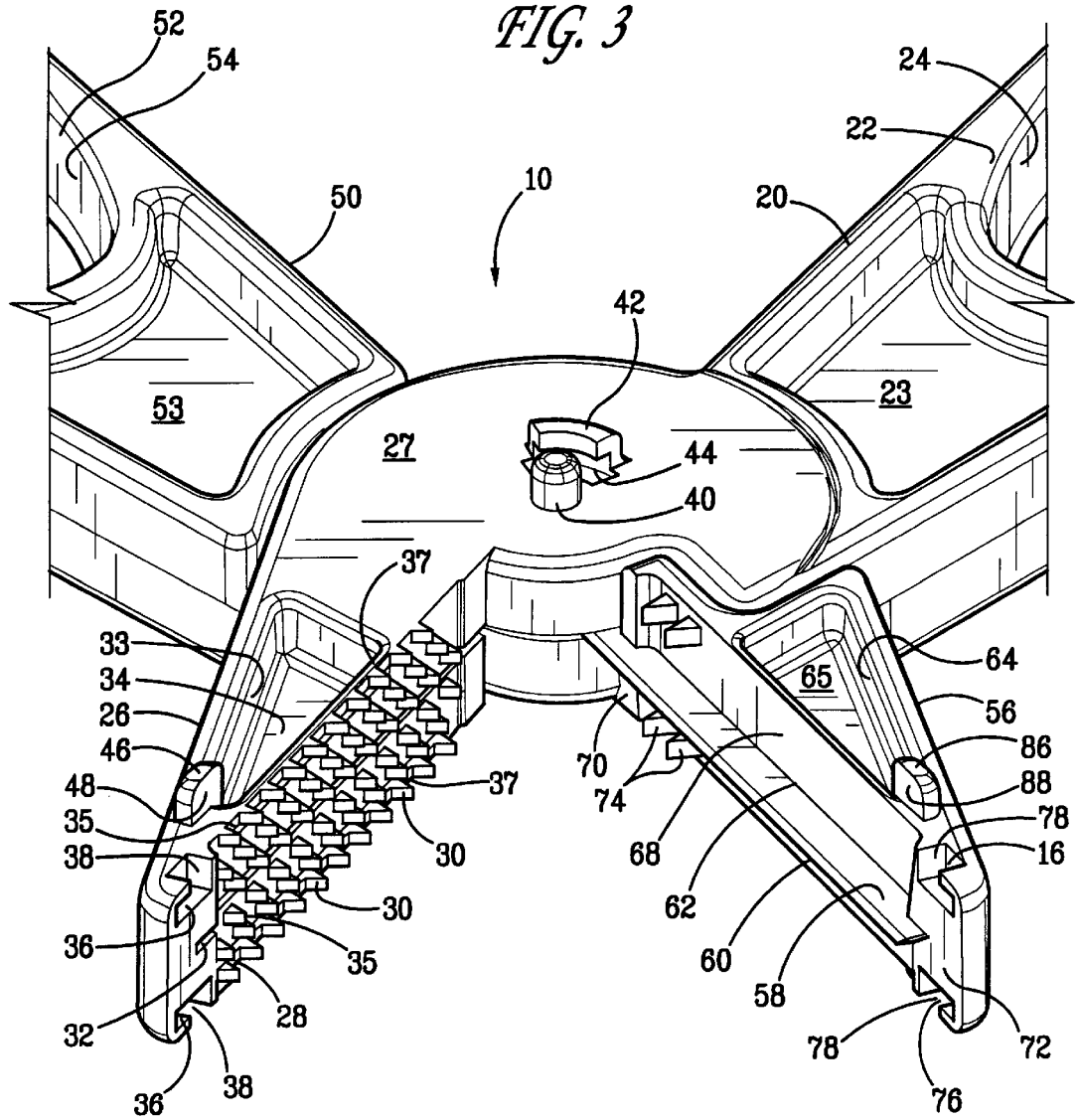

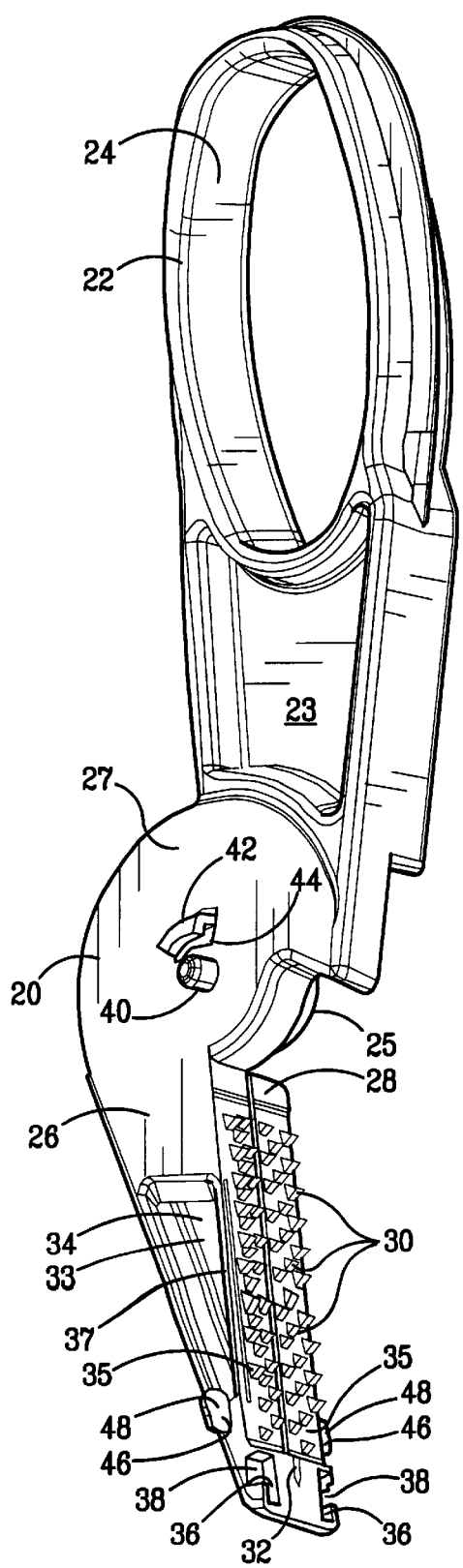

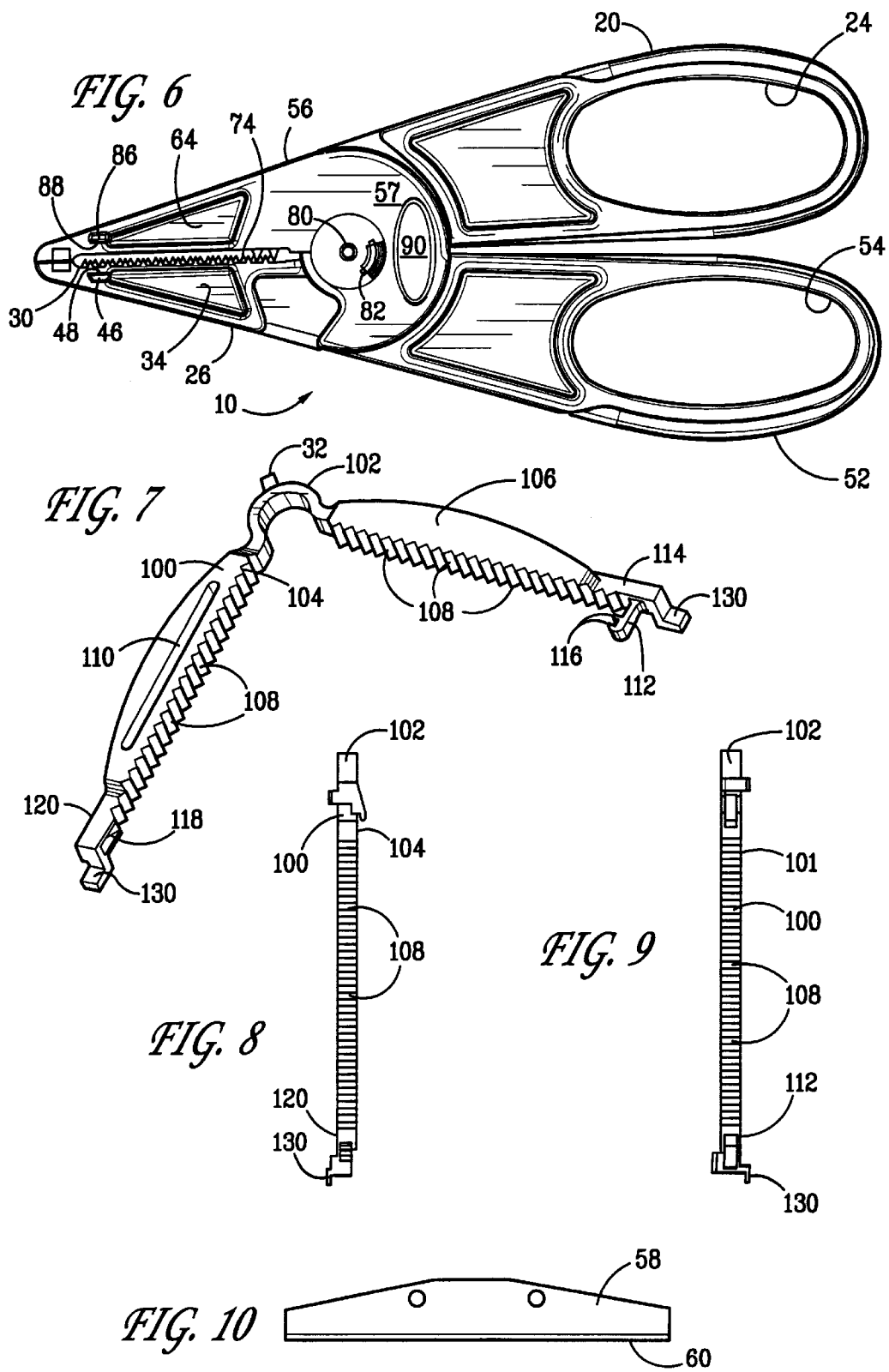

2

UMBILICAL CORD CUTTING AND CLAMPING DEVICE

BACKGROUND OF THE INVENTION

1. Field of the Invention

The present invention relates generally to obstetrical instruments and more particularly to a device for simultaneously cutting and clamping an umbilical cord and to clips for use in combination with the device.

2. Brief Description of the Prior Art

Complications occur in approximately five percent of the hospital deliveries of infants. Such complications can include having the umbilical cord wrapped around the baby's neck. In this difficult moment the baby is struggling to breathe, and the doctor is attempting to cut and clamp the umbilical cord. The cutting and clamping of the umbilical cord as soon as possible in these situations is an important factor for the life of the newborn, and the prevention of brain damage secondary to hypoxia. The conventional technique is to use clamps on the umbilical cord, and to cut between them with scissors. However, this technique wastes valuable time at a critical point in the delivery of the newborn. There is a need for a device that would save valuable time and reduce bleeding and infection such as AIDS or hepatitis.

Surgical instruments for simultaneously severing and clamping the umbilical cord of a newborn infant are known. For example, U.S. Pat. Nos. 640,517, 2,052,870, 2,060,724, 3,166,071, and 4,428,374 each disclose clamping devices for simultaneously cutting the umbilical cord and clamping both the maternal and the fetal ends of the severed cord. The devices generally employ a pair of clamps that are detachable or removal from the clamping device after the cord has been severed or clamped.

U.S. Pat. No. 3,631,858 discloses a device for simultaneously clamping and severing the umbilical cord in a single operation requiring only one hand, no detachable clamps being employed. U.S. Pat. No. 4,648,401 discloses a scissors like surgical instrument for severing an umbilical cord employing a single umbilical cord clamp and a single use, disposable blade assembly to separate the cord. The instrument permits the release of the clamp or the hemostat on the maternal end of the umbilical cord immediately after the cord is cut for collection of a blood specimen for fetal Rh factor screen test to avoid discomforting the infant by obtaining the specimen directly from the infant.

The prior art devices generally share a common disadvantage in that they are adapted for use in severing and clamping umbilical cords having a relatively small diameter. However, in obstetrical practice the range in diameter of the umbilical cords encountered is substantial (e.g. about 1–2.5 cm). Thus, the prior art devices are generally not suitable for severing in clamping cords having relatively large parameters. Umbilical cords include tough, gelatinous, fibrous tissue, as well as two arteries and one vein, and successful devices must provide sufficient force to cleanly severe them. An example of a prior art device adapted to exert substantial force for severing large umbilical cords is disclosed in my U.S. Pat. Nos. 4,870,965 and 5,009,657.

A further disadvantage of some prior art devices is that they may not securely grip on the surface of the umbilical cord. The umbilical cord of the newborn infant has a very slippery surface. Because it is covered with Wharton's jelly, a jelly-like substance, the cord is slippery and consequently very difficult to grasp and cut. Thus, when a conventional scissors-like device is closed upon the surface of the cord, the cord may be pushed out from between the blades of the device.

Some prior art devices provide teeth on both the upper and lower surfaces of the clamping jaws to securely hold the umbilical cord while the cord is being cut. Alternatively, it is known to provide teeth on both the upper and lower arms of detachable clips, and to securely hold such clips within the cutting and clamping device while the cord is being cut. The teeth immobilize the cord in place while it is being cut. Nevertheless, substantial force is required to sever a cord immobilized in this way.

There is a continuing need for an umbilical cord cutting and clamping device which can be used to quickly, easily and securely cut and clamp the full range of cords encountered in obstetrical practice.

SUMMARY OF THE INVENTION

The present invention provides an umbilical cord cutting and clamping device for severing an umbilical cord to form a maternal cord end and a fetal cord end. The device is adapted for use with clips for clamping the fetal cord end and the maternal cord end. The device advantageously provides an umbilical cord cutting and clamping device which can be used to quickly, easily and securely cut and clamp the full range of cords encountered in obstetrical practice in one second.

The device includes a pair of integral jaw-and-handle means or sections. The first or pressure jaw-and-handle means includes an integrally formed first handle and a pressure or lower jaw, and the second or blade jaw-and-handle means includes a second handle and a severing or upper jaw. The two jaw-and-handle means are pivotably affixed to each other by a pivot means and adapted to be rotated from a first or open position to a second or closed position for engaging an umbilical cord between the pressure jaw and the severing or blade jaw.

The pressure jaw includes an inner surface adapted to engage a first side of the umbilical cord. The inner surface of the pressure jaw has a plurality of teeth for grasping the first side of the umbilical cord as the umbilical cord is being severed. The teeth are spaced along the inner surface of the pressure jaw, preferably in a uniform manner.

The severing jaw or blade includes a blade or severing means for severing the umbilical cord, and an inner surface adapted to engage a second side of the umbilical cord.

The inner surface of the severing jaw extends from a first or inner end proximate the pivot means to a second or outer end. The inner surface of the severing jaw has teeth proximate the first end of the inner surface of the severing jaw for grasping one end of the second side of the umbilical cord as the umbilical cord is being severed.

Advantageously, the teeth on the inner surface of the severing jaw do not extend along the inner surface of the severing jaw. In operation, the umbilical cord is placed between the open jaws of the device, and the device is closed. As the device closes, the lower side of the umbilical cord is engaged and grasped by the teeth spaced along the inner surface of the pressure jaw. Similarly, the upper side of the umbilical cord is initially grasped by the teeth provided proximate the first end of the inner surface of the severing jaw. However, as the device is closed, the upper surface of the umbilical cord is deformed and rolls outward as the blade is severing the cord. This reduces the amount of force required to cut the cord, and makes the cutting operation smoother and easier. At the same time, the cord is securely retained in the device by the teeth spaced along the inner surface of the pressure jaw and the teeth provided on the inner surface of the severing jaw.

Preferably, at least one jaw includes at least one recess adapted to permit the inner surface of at least one jaw to flex as an umbilical cord is being clamped and cut. This further reduces the amount of force required to sever the cord. The aperture can be formed in the pressure jaw, the severing jaw, or both.

Preferably, the pressure jaw includes a pair of bilaterally symmetric recesses adapted to permit the inner surface of the pressure jaw to flex. Preferably, the inner surface of the pressure jaw is provided with a pair of longitudinally extending slots. Each slot extends from the inner surface of the pressure jaw to a respective recess thereby forming a pair of strips or cushions at the exterior lateral edges of the inner surface of the pressure jaw. When the umbilical cord is being cut, the cushions permit the inner surface of the pressure jaw to flex.

Preferably, the device further includes a first mounting means for releasably mounting a detachable fetal cord end clip, and a second mounting means for releasably mounting a detachable maternal cord end clip. The clips are preferably securely mounted on the device on either side of the jaws when the device is in the open position. When the device is closed on an umbilical cord, the clips are locked onto the severed portions of the cord proximate either end, and easily disengage from the cutting and clamping device.

The clips preferably include a pair of elongated arms extending from a central section having an opening formed therein. Each arm has an outer end and a plurality of teeth formed thereon for grasping the umbilical cord. Each arm also has lock means formed proximate the outer end thereof for locking together the clip when the clip is closed around the umbilical cord. Preferably, at least one clip arm includes an aperture formed therein for cushioning the force exerted on the umbilical cord when the clip is closed on the umbilical cord. It is also preferred that the central section of the clip include a clip positioning means for retaining the clip in the device until the cord end has been clamped.

Preferably, the device includes first support means for supporting and positioning the outer end of a first arm of the clip, a second support means for supporting and positioning the outer end of the second arm, and a rear retention means for supporting and positioning the central section. The first and second support means and the retention means are adapted to support and position the clip until the cord end has been clamped by the clip.

BRIEF DESCRIPTION OF THE DRAWINGS

FIG. 3 is a perspective view of the umbilical cord cutting and clamping device of FIG. 1 shown in an open configuration.

FIG. 4 is a perspective view of a first jaw-and-handle means of the umbilical cord and clamping device of FIG. 1.

FIG. 5 is a perspective view of a second jaw-and-handle means of the umbilical cord and clamping device of FIG. 1.

FIG. 6 is a side elevational view of a second embodiment of umbilical cord cutting and clamping devices of the present invention.

FIG. 7 is a perspective view of a clip for use in the umbilical cord cutting clamping device of the present invention shown in an open configuration.

FIG. 8 is a side elevational view of the clip of FIG. 7.

FIG. 9 is a second side elevational view of the clip of FIG. 7.

FIG. 10 is a side elevational view of a cutting blade mounted in the umbilical cord cutting and clamping device of FIG. 1.

DETAILED DESCRIPTION

Figure 1:
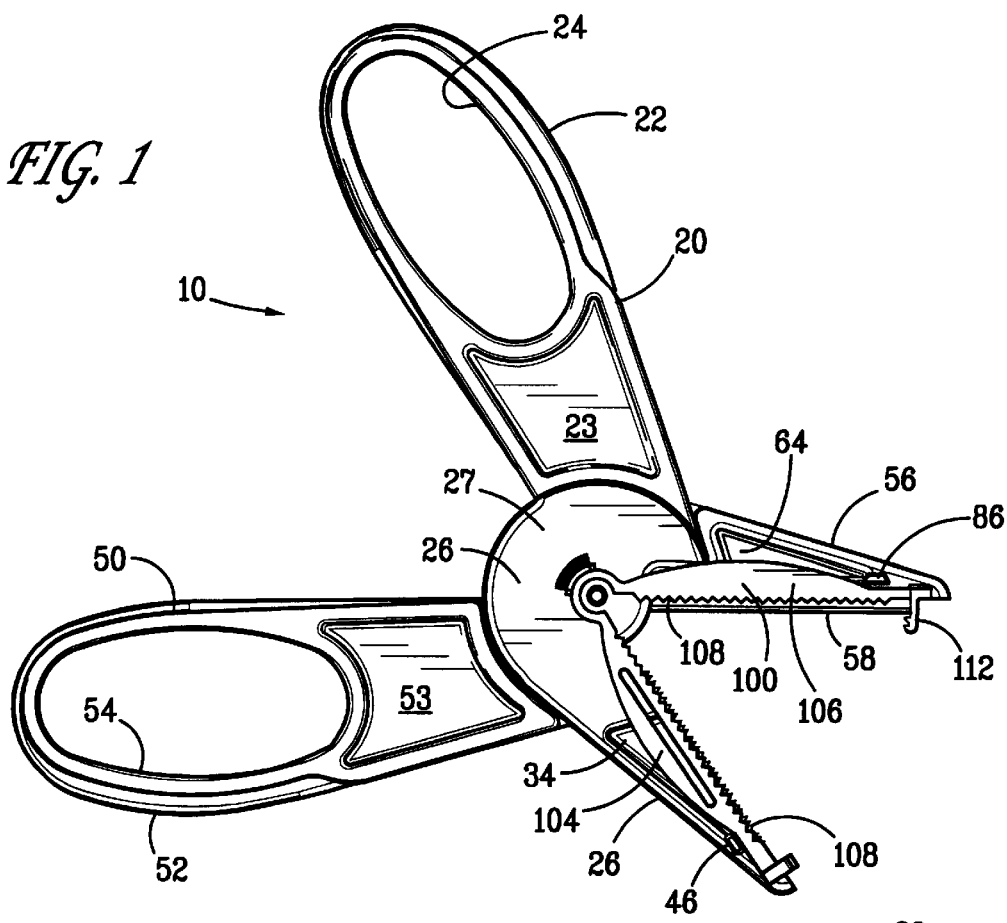
FIG. 1 is a side elevational view of a presently preferred embodiment of an umbilical cord cutting and clamping device according to the present invention depicted in an open position.

Referring now to the drawings in detail, wherein like reference numerals indicate like elements in each of the several views, reference is first made to FIG. 1, wherein an umbilical cord cutting and clamping device 10 according to the present invention is shown. The device 10 includes a first integrally formed jaw-and-handle means or device half 20 having an ergonomically formed first handle 22 at one end thereof. The first handle 22 is provided with an opening 24 for receiving one or more fingers of the user so that the device 10 can be comfortably and securely grasped by a single hand of the user. The first jaw-and-handle means 20 also includes a lower or pressure jaw 26 integrally formed with the first handle 22. The device 10 further includes a second integrally formed jaw-and-handle means or second device half 50 having a ergonomically formed second handle 52 similarly provided with an opening 54 for receiving one or more fingers of a user. Each handle 22, 52 also includes a pair of recesses 23, 53 formed in the exterior side surfaces thereof for increasing the strength and rigidity of the respective handle 22, 52. The second jaw-and-handle means 50 also includes an integrally formed severing or upper jaw 56 having a severing means or blade 58 mounted therein for severing an umbilical cord. The blade 58 (best seen in FIG. 10) is preferably formed from a rigid, sharpenable material such as stainless steel, has a sharpened edge 60 and is securely mounted in a slot or recess 62 formed in the upper jaw 56 (FIG. 3).

The first and second jaw-and-handle means 20, 50 are rotatably affixed to one another to provide a pivot axis for the device 10.

The device 10 and its associated clamps are preferably formed from a strong, substantially rigid material which is capable of transmitting sufficient force to cleanly sever the umbilical cord. The material should have sufficient thermal stability and/or solvent resistance to be easily sterilizable by conventional methods. For example, most of the components of the device 10 and the associated clamps can be fabricated from a suitable grade of polypropylene or polycarbonate material, by injection molding or some similar process. The device 10 can be manufactured so that it can be discarded after a single use. It can not be used again. It will not function after one use. The device 10 can be sterilized after manufacture, packaged in a sterile package and discarded after use.

Figure 2:
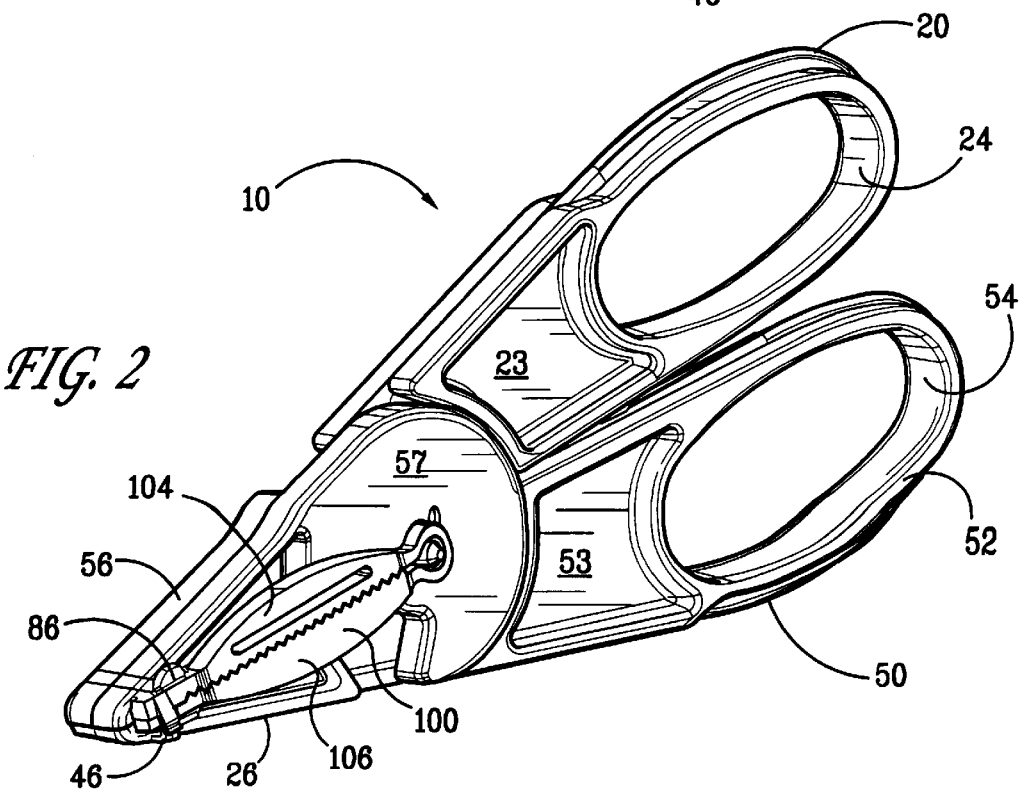
FIG. 2 is a perspective view of the umbilical cord cutting and clamping device of FIG. 1 shown in a closed position.

The device 10 is adapted to be rotated by the user from a first or open position (FIGS. 1 and 3) to a second or closed position (FIGS. 2 and 6). Each jaw 26, 56 is provided with a generally planar central section 27, 57 having a thickness of approximately half that of the remaining portions of each jaw-and-handle means 20, 50 and adapted to engage and mount on the complementary central section 57, 27 of the other jaw 56, 26, by means of a generally circular mounting lug 25 (FIG. 4) formed on the inner surface of the central section 27 of the lower jaw 26 and a corresponding recess formed in the inner surface of the central section 57 of the upper jaw 56 (not shown), each formed to permit substantial force to be transmitted to the jaws 26, 56 when the device 10 is closed and to maintain the alignment of the jaw-andhandle means 20, 50 as the device 10 is closed. The central sections 27, 57 are shaped (best seen in FIGS. 4, 5 and 6) to provide an exterior peripheral surface for contact with a corresponding surface on the other jaw 56, 26 when the device 10 is in a fully open position.

When the device 10 is in the open position, a clip 100 is mounted on one or both sides of the jaws 20, 50 of the device 10 (FIG. 1), as described below. The user places the open jaws 20, 50 of the device 10 over an umbilical cord (not shown), and the user closes the handles 22, 52 of the device 10 together. As the jaws 20, 50 of the device 10 close, the blade 58 severs the umbilical cord and the clip or clips 100 clamps the cut ends of the cord, which are then released from the device 10.

As best seen in FIG. 3, the lower or pressure jaw 26 has a generally planar inner surface 28 and the upper or severing jaw 56 has a similar generally planar inner surface 68. As can be seen in FIGS. 2 and 6, the inner surfaces 28, 68 of the lower and upper jaw 26, 56 are opposed and generally coplanar when the device 10 is in the closed position. The lower jaw 26 includes a plurality of teeth 30 (FIGS. 3 and 4) formed therein for grasping the first or lower side or surface of the umbilical cord and prevent the cord from slipping to the front part of the pressure jaw. The generally triangular teeth 30 are arranged in several rows along the inner surface 28 of the lower jaw 26 and spaced along the entire inner surface 28. A groove or recess 32 is formed along the center line of the lower jaw 26 in the inner surface 28 of the lower jaw 26 for receiving the blade 58 when the device 10 is closed.

The inner surface 68 of the upper jaw 56 (FIGS. 3 and 5) extends from a first or inner end 70 proximate the handle 50 to a second or outer end 72. The inner surface 68 of the upper jaw 56 includes a plurality of teeth 74 for grasping the upper or second side or surface of the umbilical cord. However, unlike the teeth 30 of the lower jaw 26, the teeth 74 of the upper jaw 56 are positioned proximate the inner end 72 of the inner surface 68 of the upper jaw 56, and not spaced along the inner surface 68 of the upper jaw 56. Advantageously, when the device 10 is operated to sever an umbilical cord, the teeth 74 of the upper jaw 56 first engage one end of the upper side of the umbilical cord to help retain the umbilical cord between the jaws 26, 56 of the device 10 as the device 10 is being closed. However, as the device 10 is closed, the upper surface of the umbilical cord is otherwise unrestrained and can be freely deformed by the action of the blade 58 as the blade 58 severs the cord. This action permits the cord to be cut more efficiently and smoothly compared with prior art devices which provide teeth spaced along both the lower and upper jaws.

Each of the upper and lower jaws 26, 56 has a pair of generally triangular opposed recesses 33, 64 (FIGS. 3, 4, 5) formed in the jaw 26, 56 beneath the respective inner surface 28, 68. Only one recess 33, 64 of each bilaterally symmetric pair is visible in each figure. Each of the pairs of recesses 33, 64 has a respective thin wall 34, 65 formed in the respective jaw 26, 56 separating the respective recesses 33, 64 of each pair.

As best seen in FIG. 4, the inner surface 28 of the pressure jaw 26 is provided with a pair of longitudinal slots 35 preferably extending adjacent the exterior edge of the inner surface 28 from the inner surface 28 to the respective triangular recesses 33. The slots 35 delimit a pair of strips or cushions 36 formed in the inner surface 28 to permit the inner surface 28 to deform slightly to conform to the shape of the umbilical cord as the umbilical cord is being cut in the device 10. This permits umbilical cords of various diameters, including large diameter cords, to be cut by the device 10 of the present invention, and cushions the cutting action of the device 10 for smoother and more efficient operation. Preferably, as shown in FIG. 4, the cushions 36 are formed close to the lateral edges of the inner surface 28 of the pressure jaw 26 and do not include any teeth 30. However, the slots 35 can, in the alternative, be formed between rows of teeth, such as the first and second rows of teeth 30 (FIG. 3) so the cushions 37 defined by the slots 35 include one or more rows of teeth 30.

A suitable cord end clamping means or clip 100 for use in the device 10 is illustrated in FIGS. 7–9 and shown mounted in the device 10 in FIGS. 1 and 2. The clip 100 includes an arcuate central section 102 having a first clamp arm 104 and a second clamp arm 106 extending therefrom. The inner surfaces of the first clamp arm 104 and the second clamp arm 106 have a plurality of teeth 108 for holding the severed end of the umbilical cord. The first clamp arm 104 has an elongated aperture 110 formed therein beneath the inner surface thereof so that the inner surface of the clamp arm 104 can deform slightly to conform to the shape of the umbilical cord as the umbilical cord is being clamped by the clip 100, thereby providing a cushioning effect. The second clamp arm 106 can also optionally include an aperture for like purpose (not shown). An inwardly directed locking tab 112 is provided proximate the outer end 114 of the second clamp arm 106. The locking tab 112 has a pair of protrusions or projections 116 extending in the plane defined by the clamp arms 104, 106. A lock aperture 118 is formed in the outer end 120 of the first clamp arm 104 opposite the central section 102. The locking tab 112 is sized and positioned to be securely received within the lock aperture 118 when the clip 100 is closed, and the pair of protrusions 116 define lock positions for the clip 100.

As best seen in FIG. 7, the clip 100 is provided with means for mounting the clip 100 on the device 10 in the form of a pair of hooks or first and second mounting tabs 130 formed at the respective outer ends 120, 114 of the first and second clamp arms 104, 106 and a third mounting tab 132 extending outwardly from the central section 102. The hooks 130 are adapted to be received within generally rectangular pockets 36, 76 formed in the inner surfaces 28, 68 of the lower and upper jaws 26, 56, best seen in FIG. 3, proximate the outer ends of the jaws 26, 56. A pair of hook pockets 36 is formed proximate either side of the jaws 26, 56 so that two clips 100 can be mounted on the device 10 if desired, or a single clip 100 can be mounted on either side of the device 10. Each hook pocket 36, 76 is accessible from a respective side of the device 10 through a generally rectangular access opening 38, 78 formed in the side of the respective jaw 26, 56, with the hook pocket 36, 76 extending within the respective jaw 26, 56 outwardly beyond the respective access opening 38, 78. When the clip 100 is mounted on a side of the device 10, the hooks 130 and the hook pockets 36, 76 are adapted so that the hooks 130 are received within the hook pockets 36, 76. The clip 100 is preferably formed so that the clip 100 must be compressed slightly for the clip 100 to be mounted on the device 10, and the corresponding spring force of the clip 100 retains the hooks 130 securely in the hook pockets 36, 76. When the device 10 has been closed around an umbilical cord, the clamp arms 104, 106 of the clip 100 extend around the umbilical cord ends (not shown), and the projection of the clamp arms 104, 106 along the length of the inner surfaces 28, 68 of the jaws 26, 56 of the device 10 shortens compared with the projection of the clamp arms 104, 106 of the clip 100 when the device is in the open position. The mounting tabs or hooks 130 can then freely pass through the access openings 38, 78 formed in the sides of the respective jaws 26, 56 for releasing the cut, clamped cord end from the device 10.

Each of the jaws 26, 56 has an outwardly extending mounting post 40, 80 formed on the side thereof proximate the pivot axis of the device 10 for receiving the central section 102 of a clip 100 when a clip 100 is mounted on a side of the device 10. Each of the jaws 26, 56 also includes a generally arcuate clip retention tab 42, 82 formed in the respective side thereof proximate the mounting post 40, 80 and extending above the surface of the jaw side for retaining the third mounting tab 132 of the clip 100 until the device 10 is in the closed position. In addition, a generally arcuate recess 44, 84 is formed adjacent each mounting post 40, 80 under the respective clip retention tab 42, 82, the recess 44, 84 preferably being formed so that as the device 10 is rotated from an open to a closed position, the third mounting tab 132 of the clip 100 is cammed upward and out from under the retention tab 42 so that the clip 100 clamping the cut cord end can be easily detached from the device 10 after the cord has been cut by the device 10 and clamped by the clip 100.

Each of the jaws 26, 56 are also provided with a pair of support pillows 46, 86 extending from the respective sides thereof proximate the hook pockets 36, 76 and positioned to support a respective clamp arm 104, 106 of a clip 100 while the clip 100 is being closed to clamp a cord end (best seen in FIGS. 3–5). The support pillows 46, 86 have a generally planar inner surface 48, 88 for engaging and supporting the respective clamp arm 104, 106 when the clip 100 is mounted in the device 10 when the device is in the open position. When the device 10 is being closed, force is transmitted primarily through the jaws 26, 56 and the support pillows to the clamp arms 46, 86 of the clip 100 to force the clamp arms 104, 106 around the umbilical cord end.

Optionally, a removable plaque 90 bearing indicia can be affixed to the central section 27 of the lower jaw 22 (FIG. 6).

Various other modifications can be made in the details of the various embodiments of the apparatus of the present invention, all within the scope and spirit of the invention and defined by the appended claims. For example, the device 10 can include the lever-assisted clamping means disclosed in my U.S. Pat. No. 4,870,965, which is incorporated by reference herein. Similarly, the device 10 can include a central pivot member, such as disclosed in my U.S. Pat. No. 5,009,657, similarly incorporated herein by reference. Further variations of my presently claimed invention will be apparent to those skilled in the art.

I claim:

1. An umbilical cord cutting and clamping device for severing an umbilical cord to form a maternal cord end and a fetal cord end, the device comprising:
    a) an integral first jaw-and-handle means, the first jaw-and-handle means including a first handle and a pressure jaw;
    b) an integral second jaw-and-handle means, the second jaw-and-handle means including a second handle and a severing jaw, the first jaw-and-handle means being pivotably affixed to the second jaw-and-handle means for engaging an umbilical cord between the pressure jaw and the severing jaw;
    the pressure jaw including an inner surface adapted to engage a first side of the umbilical cord, the inner surface of the pressure jaw including a plurality of teeth spaced along the inner surface of the pressure jaw for grasping the first side of the umbilical cord as the umbilical cord is being severed;
    the severing jaw including a severing means for severing the umbilical cord and an inner surface adapted to engage a second side of the umbilical cord, the inner surface of the severing jaw extending from a first end to a second end, the inner surface of the severing jaw having teeth proximate the first end of the inner surface of the severing jaw for grasping one end of the second side of the umbilical cord as the umbilical cord is being severed; and
    wherein at least one jaw includes at least one recess adapted to permit the inner surface of the at least one jaw to flex as an umbilical cord is being clamped and cut.

2. A device according to claim 1 wherein the pressure jaw includes a pair of bilaterally symmetric recesses adapted to permit the inner surface of the pressure jaw to flex as an umbilical cord is being clamped and cut.

3. A device according to claim 1 wherein the pressure jaw includes a pair of longitudinally extending slots extending from the inner surface of the pressure jaw to a respective recess, forming a pair of cushions in the inner surface adapted to permit the inner surface of the pressure jaw to flex as an umbilical cord is being clamped and cut.

4. A device according to claim 1 further including first mounting means for releasably mounting a detachable fetal cord end clip.

5. A device according to claim 1 further including second mounting means for releasably mounting a detachable maternal cord end clip.

6. In combination, an umbilical cord cutting and clamping device for severing an umbilical cord to form a maternal cord end and a fetal cord end, and at least one clip for clamping at least one of the maternal cord end and the fetal cord;
    the device comprising:
    a) an integral first jaw-and-handle means, the first jaw-and-handle means including a first handle and a pressure jaw;
    b) an integral second jaw-and-handle means, the second jaw-and-handle means including a second handle and a severing jaw, the first jaw-and-handle means being pivotably affixed to the second jaw-and-handle means for engaging an umbilical cord between the pressure jaw and the severing jaw;
    the pressure jaw including an inner surface adapted to engage a first side of the umbilical cord, the inner surface of the pressure jaw including a plurality of teeth spaced along the inner surface of the pressure jaw for grasping the first side of the umbilical cord as the umbilical cord is being severed;
    the severing jaw including a severing means for severing the umbilical cord and an inner surface adapted to engage a second side of the umbilical cord, the inner surface of the severing jaw extending from a first end to a second end, the inner surface of the severing jaw having teeth proximate the first end of the inner surface of the severing jaw for grasping one end of the second side of the umbilical cord as the umbilical cord is being severed, and
    wherein at least one jaw includes at least one recess adapted to permit the inner surface of the at least one jaw to flex as an umbilical cord is being clamped and cut.

7. A device according to claim 6 wherein the pressure jaw includes a pair of bilaterally symmetric recesses adapted to permit the inner surface of the pressure jaw to flex as an umbilical cord is being clamped and cut.

8. A device according to claim 6 wherein the pressure jaw includes a pair of longitudinally extending slots extending from the inner surface of the pressure jaw to a respective recess, forming a pair of cushions in the inner surface adapted to permit the inner surface of the pressure jaw to flex as an umbilical cord is being clamped and cut.

9. A device according to claim 6 further including first mounting means for releasably mounting a detachable fetal cord end clip.

10. A device according to claim 6 further including second mounting means for releasably mounting a detachable maternal cord end clip.

11. A combination according to claim 6 wherein the at least one clip comprises a pair of elongated arms extending from a central section having an opening formed there, each arm having an outer end and a plurality of teeth formed thereon for grasping the umbilical cord, each arm having lock means formed proximate the outer end thereof for locking together the clip when the clip is closed around the umbilical cord.

12. A combination according to claim 11 wherein at least one clip arm includes an aperture formed therein for cushioning the force exerted on the umbilical cord when the clip is closed on the umbilical cord.

13. A combination according to claim 11 wherein the central section of the clip includes clip positioning means for retaining the clip in the device until the cord end has been clamped.

14. A combination according to claim 11 wherein the device includes first support means for supporting and positioning the outer end of a first arm of the at least one clip, a second support means for supporting and positioning the outer end of the second arm of the at least one clip, and a rear retention means for supporting and positioning the central section of the at least one clip, the first and second support means and the retention means being adapted to support and position the at least one clip until the cord end has been clamped by the clip.

* * * * *